US006770013B2

(12) United States Patent
Stillinger

(10) Patent No.: US 6,770,013 B2
(45) Date of Patent: Aug. 3, 2004

(54) ISOMETRIC EXERCISE DEVICE

(75) Inventor: Scott H. Stillinger, Monte Sereno, CA (US)

(73) Assignee: Acorn Products, LLC, Monte Sereno, CA (US)

(*) Notice: Subject to any disclaimer, the term of this patent is extended or adjusted under 35 U.S.C. 154(b) by 0 days.

(21) Appl. No.: 10/136,062

(22) Filed: Apr. 29, 2002

(65) Prior Publication Data

US 2003/0203795 A1 Oct. 30, 2003

(51) Int. Cl.$^7$ .................... A63B 21/002; A63B 23/02; A61F 5/00

(52) U.S. Cl. .................... 482/91; 482/131; 482/145; 482/907; 606/241

(58) Field of Search .................... 482/79, 91, 92, 482/125, 126, 131, 140, 145, 148, 907; 606/241, 237; 602/32, 36, 38; 601/23

(56) References Cited

U.S. PATENT DOCUMENTS

| | | | | | |
|---|---|---|---|---|---|
| 1,508,892 | A | * | 9/1924 | Mikalsen | 482/131 |
| 2,815,022 | A | | 12/1957 | Krumm | |
| 3,094,324 | A | * | 6/1963 | Shingleton | 482/131 |
| 3,134,379 | A | | 5/1964 | Nightingale | |
| 3,966,200 | A | | 6/1976 | Kirk | |
| 4,398,713 | A | | 8/1983 | Ellis | |
| 4,445,684 | A | | 5/1984 | Ruff | |
| 4,470,408 | A | | 9/1984 | Gordon | |
| 4,494,532 | A | * | 1/1985 | Masuda et al. | 482/38 |
| 4,534,555 | A | | 8/1985 | McGowen | |
| 4,608,971 | A | | 9/1986 | Borschneck | |
| 4,641,637 | A | | 2/1987 | Rosen | |
| 4,647,040 | A | | 3/1987 | Ehrenfried | |
| 4,834,364 | A | * | 5/1989 | Gongwer et al. | 482/131 |
| 5,106,083 | A | * | 4/1992 | Hall | 482/145 |
| 5,575,745 | A | * | 11/1996 | Lin | 482/144 |
| 5,718,660 | A | * | 2/1998 | Chen | 482/144 |
| 5,971,902 | A | * | 10/1999 | Robertson et al. | 482/142 |
| 6,007,507 | A | * | 12/1999 | Ledany | 602/32 |
| 6,030,325 | A | * | 2/2000 | Ottoson et al. | 482/144 |
| 6,186,968 | B1 | * | 2/2001 | Wu | 602/32 |
| 6,428,496 | B1 | * | 8/2002 | Sargent | 602/32 |

FOREIGN PATENT DOCUMENTS

| | | | | |
|---|---|---|---|---|
| DE | 1278698 | | | 9/1968 |
| DE | 3234687 | | | 3/1984 |
| EP | 106304 | A2 | * | 4/1984 |
| FR | 2446109 | | | 1/1979 |
| WO | WO 94/04227 | | * | 3/1994 |

* cited by examiner

*Primary Examiner*—Nicholas D. Lucchesi
*Assistant Examiner*—Victor Hwang
(74) *Attorney, Agent, or Firm*—Kolisch Hartwell, P.C.

(57) ABSTRACT

A device for selectively applying tractive forces to a user's back. In some embodiments, the device is an isometric exercise device. In some embodiments, the device is a portable, collapsible device. In some embodiments, the device enables a user to selectively adjust and control the magnitude and/or application region of the tractive forces while the device is being used. In some embodiments, the user-exerted tractive force is applied to handle portions of the device and transmitted to a lower extremity engaging portion of the device. In some embodiments, the device is configured such that a user can connect and remove the user's lower extremities from the device without requiring the manual manipulation of the mounts used to selectively retain the user's lower extremities. In some embodiments, the device is adjustable for use by a wide variety of differently sized individuals.

52 Claims, 11 Drawing Sheets

ISOMETRIC EXERCISE DEVICE

FIELD OF THE INVENTION

The present invention relates generally to isometric exercise devices, and more specifically to devices that apply tractive forces to a user's spine.

BACKGROUND OF THE INVENTION

Individuals who suffer from back pain, and particularly from low back pain, may often obtain relief from such pain by the application of a tractive, spine-extending force. Such force normally involves immobilizing the individual's neck and shoulders and applying a force to the individual's lower extremities. The force is generally applied using a hospital-type bed equipped with a tractive force creating mechanism. Another known instrument for applying such a force is an inversion apparatus, which essentially suspends an individual in an inverted position wherein the individual literally hangs by the user's feet or ankles.

The drawback of the traction-equipped bed is that the individual undergoing treatment cannot adjust the tractive force applied after the individual has been strapped into the bed. The inversion technique applies a force that is determined by the weight of the individual, which may be more or less force than the individual needs to extend their spine. Additionally, the inversion technique is uncomfortable if used soon after a meal and is always somewhat uncomfortable because it tends to cause excessive blood pressure in the individual's head.

SUMMARY OF THE INVENTION

The present invention is directed to a device for selectively applying tractive forces to a user's back. In some embodiments, the device is an isometric exercise device. In some embodiments, the device is a portable, collapsible device. In some embodiments, the device enables a user to selectively adjust and control the magnitude and/or application region of the tractive forces while the device is being used. In some embodiments, the user-exerted tractive force is applied to handle portions of the device and transmitted to a lower extremity engaging portion of the device. In some embodiments, the device is configured such that a user can connect and remove the user's lower extremities from the device without requiring the manual manipulation of the mounts used to selectively retain the user's lower extremities. In some embodiments, the device is adjustable for use by a wide variety of differently sized individuals.

DETAILED DESCRIPTION AND BEST MODE OF THE INVENTION

Figure 1:
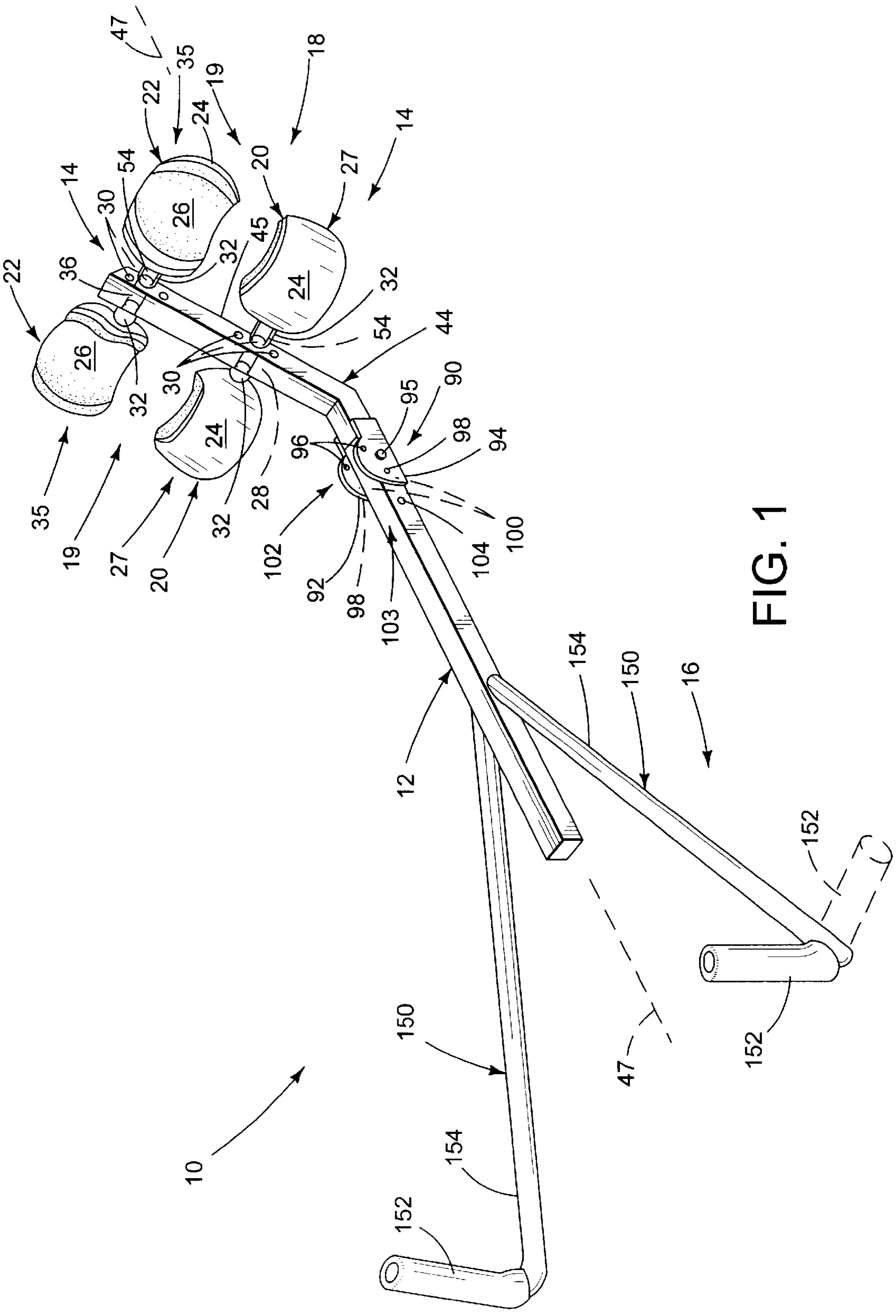
FIG. 1 is a perspective view of an isometric exercise device constructed according to the present invention, with various positions of the components of the device shown in phantom lines.
Figure 2:
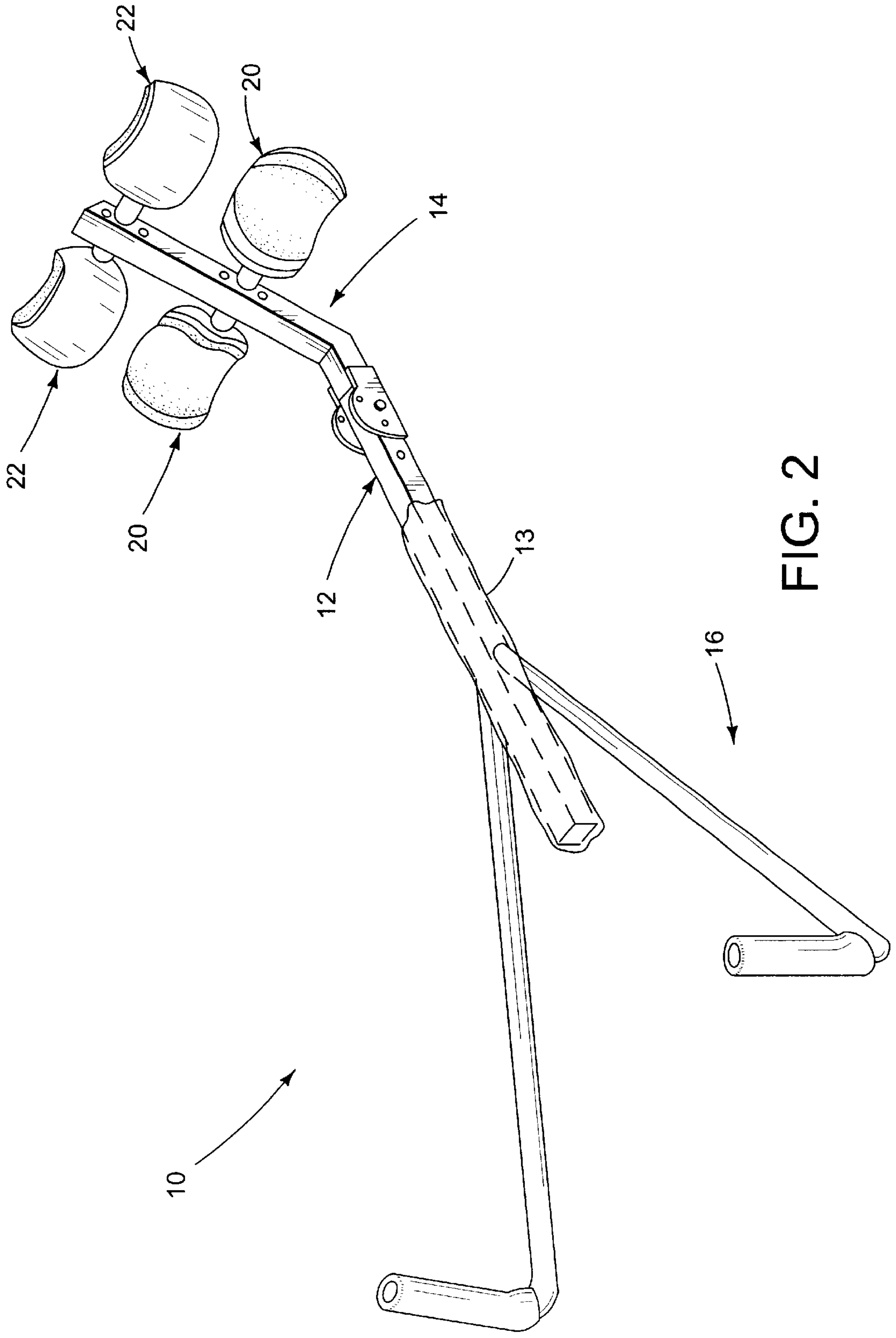
FIG. 2 is a perspective view of another isometric exercise device constructed according to the present invention.

An example of an isometric exercise device constructed according to the invention is shown in FIG. 1 and generally indicated at 10. Device 10 may also be referred to as an isometric stretching device, or a stretching device. In the illustrated embodiment, device 10 includes a body 12 to which a lower-extremity engagement structure 14 and a transmitting portion 16 are coupled. Lower-extremity engagement structure 14 and transmitting portion 16 comprise what may be referred to as a body-connecting means, or a body-connecting structure. In FIG. 1, body 12 has an elongate, generally tubular construction. It is within the scope of the invention, however, that body 12 may have a variety of configurations. For example, in some embodiments, body 12 may be a solid, non-tubular member, and in some embodiments, the body may itself form a comparatively wider and/or longer structure, such as to include supports for the underside of a user's legs. Body 12 may optionally include a cover 13 that extends generally between the illustrated portion and the user's legs. Cover 13, which is shown in fragmentary lines in FIG. 2 may be formed of any suitable deformable or resilient material and is adapted to provide a smooth and/or supportive interface with the underside of a user's legs.

Lower-extremity engagement structure 14 is adapted to receive and support a user's lower extremities, such as the user's feet, ankles and/or lower legs, and to provide comfortable, yet firm, support to these extremities as tractive forces are applied by a user. As used herein, the term "lower extremity" refers to a user's lower leg, ankle and foot, and therefore lower-extremity engagement structure 14 engages or supports at one of one these regions of a user's lower extremity. The following discussion refers to a lower-extremity engagement structure that provides two generally opposed and spaced-apart contact regions to each of the user's lower extremities. However, it is within the scope of the invention that lower-extremity engagement structure 14 may include any suitable structure for releasably engaging at least a portion of a user's lower extremities to provide resistive support thereto as tractive forces are applied by a user. Similarly, the above definition of "lower extremity," as used herein, is not meant to imply or require that each of these regions need to be received and supported by lower-extremity engagement structure 14. In some embodiments, only one region will be received and supported. In others, more than one may be engaged and supported.

In FIG. 1, structure 14 includes at least one lower extremity mount 18 for each of the user's lower extremities. Although not required in all embodiments of the invention, it is preferable that a user can insert and remove the user's lower extremities into and out of the mounts without requiring the user to adjust or otherwise manipulate the mounts with the user's hands. More specifically, it should be remembered that many users of device 10 will be experiencing back pain. Accordingly, it is desirable, but not required, that the user can use device 10, including coupling the user's lower extremities to mounts 18, without having to bend to a position in which the user's hands are positioned at or around the user's lower extremities.

The mounts shown in FIG. 1 provide an example of a lower extremity engaging means that is adapted to automatically engage the user's lower extremities. By this it is meant that a user does not have to manually adjust or secure the mounts after insertion of the user's lower extremities into an operative position therewith. As shown, each mount 18 includes a stirrup assembly 19, such as indicated in FIG. 1. Each stirrup assembly 19 is adapted to receive and support spaced-apart and generally opposed surfaces of a user's lower extremity. In the illustrated embodiment, each stirrup assembly includes a heel-engaging stirrup 20, which is adapted to receive and support a heel portion of a user's leg proximate the user's ankle. It is within the scope of the invention that stirrup 20 may additionally or alternatively receive and support the back of a user's lower leg, and as such may in those embodiments also be referred to as a leg-engaging stirrup. Each stirrup assembly also includes a foot-engaging stirrup 22, which is adapted to receive and support the top of user's foot. As shown, each stirrup includes a base 24 and a body-engaging surface 26, which is typically formed from a foamed or padded material to cushion the engagement of the user's body by the stirrup. In the illustrated embodiment, the stirrup assemblies define generally opposed concave surfaces.

As shown, the stirrups 20 and 22 in each stirrup assembly 19 are spaced-apart from each other relative to body 12, with stirrups 22 being located further away from body 12 than stirrups 20. As used herein, the heel-engaging stirrups may be referred to collectively as a heel-engaging stirrup pair 27, and the foot-engaging stirrups may be referred to collectively as a foot-engaging stirrup pair 35.

Figure 23:
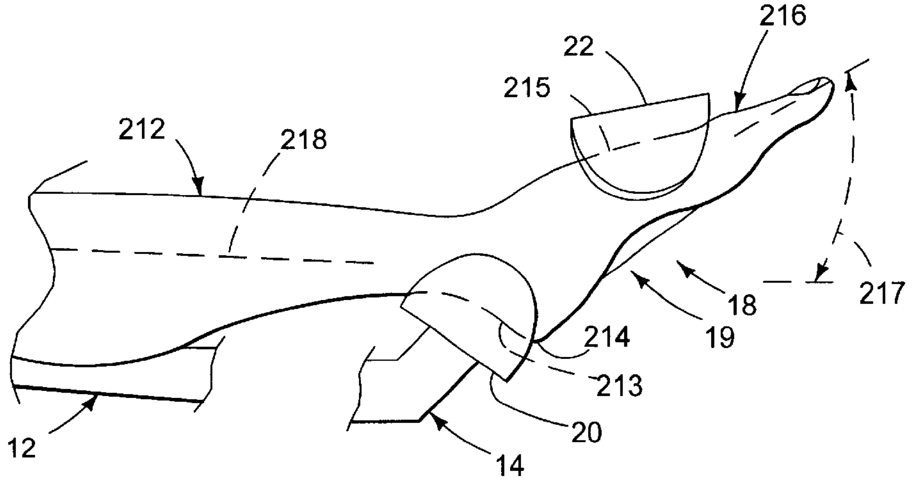
FIG. 23 is a fragmentary side-elevation view of the device of FIG. 1 or 17 being used to support a user's lower extremity.

In FIG. 23, a user's lower extremity 212 is shown received in an operative position within stirrup assembly 19. As shown, the back 213 of the user's heel region 214 is received and supported by stirrup 20, and the top 215 of the user's foot 216 is received and supported by stirrup 22. In the illustrated configuration, mount 18, namely stirrup assembly 19, supports the user's foot in a relaxed position, in which the user's foot and toes extend at an angle 217 in the range of approximately 25 and approximately 40 degrees relative to the long axis 218 of the user's leg, with a specific orientation of approximately 30–35 degrees shown in FIG. 23. It is within the scope of the invention that other angles may be used, such as (but not limited to) angles in the range of approximately 15 and approximately 110 degrees, of approximately 20 and approximately 90 degrees, and of approximately 20 and approximately 70 degrees.

A benefit of the configuration shown in FIG. 23 is that a user's lower extremities may be inserted into an operative position with the device without requiring the use of the user's hands. More specifically, the stirrups in each stirrup assembly are oriented such that neither stirrup defines a closed loop, such as a strap or cuff that must be secured and/or tightened around a user's leg after insertion of the user's leg therethrough. Instead, by inserting the user's lower extremity above the heel-engaging stirrup and below the foot-engaging stirrup, the stirrups apply generally opposed restraining forces upon the user's lower extremity, and therefore retain the user's lower extremity without requiring the use of manually tightened straps, cuffs or the like. The illustrated embodiment also demonstrates an example of a mount that accommodates lateral insertion and removal of the user's lower extremity. More specifically, each mount enables a user to insert one of the user's lower extremities into an operative position relative to the mount by moving the user's lower extremity into this position from a disengaged position on either lateral side of the mount. Furthermore, after the user's lower extremities are inserted into an operative position, the user is not required to keep the user's feet in a flexed position to prevent the user's feet from disengaging the stirrups.

In the illustrated embodiment shown in FIG. 1, the heel-engaging and foot-engaging stirrups are respectively mounted on axles 28 and 36, which are rotatably received in bores 30 in a frame portion 44 of structure 14. Also shown are optional bushings 32 that space the stirrups relative to frame portion 44. In this configuration, the stirrups in each stirrup pair may be rotated as a unit with respect to the frame portion. In the illustrated embodiment, the region 45 of frame portion 44 to which mounts 18 are coupled extends at an angle relative to the long axis of body 12, thereby positioning the stirrups, and a user's lower extremities that are received therein, in an elevated position relative to the body. It is within the scope of the invention, however, that frame portion 44, including region 45, may have a wide variety of configurations relative to body 12, including configurations in which region 45 extends generally along the long axis 47 of body 12 and configurations in which region 45 extends generally parallel and offset from this axis.

Recognizing that devices according to the present invention may be used by a variety of users of different sizes, the distance between the stirrups 20 and 22 forming each stirrup is preferably adjustable. For example, in FIG. 1, structure 14 includes a plurality of spaced-apart bores 30 into which axles 28 and 36 may be selectively inserted to adjust the relative spacing of the axles, and corresponding stirrups, along frame portion 44. In the illustrated embodiment, at least one stirrup of each stirrup pair 27 and 35 includes a fastening mechanism 54 that enables the stirrup to be selectively released from the axle, thereby permitting removal of the corresponding axle from the bore in which it was inserted. The axle may thereafter be reinserted into a different bore to adjust the relative spacing of the stirrup pairs. An example of such a fastening mechanism 54 is shown in FIG. 1 in the form of a set screw, but other suitable mechanisms may be used, such as pins, threads, spring-biased detents, and the like. An additional or alternative reason for providing adjustability to the sizing of the mounts is that users may periodically use a device according to the invention while wearing shoes, and at other times use the device when not wearing shoes.

As discussed, the stirrups are mounted on axles, which are rotatably received within bores in structure 14. This enables the respectively leg- or foot-engaging stirrups to be rotated with their respective axles, such as to adjust to the shape of a particular user's lower extremities and/or to permit the stirrups to be rotated as a user's lower extremity is inserted into and removed from an operative position with structure 14. To illustrate that the stirrups are rotatable relative to structure 14, the stirrups are shown in FIG. 1 in a free rotated position, with an operative position shown in FIG. 2.

Figure 3:
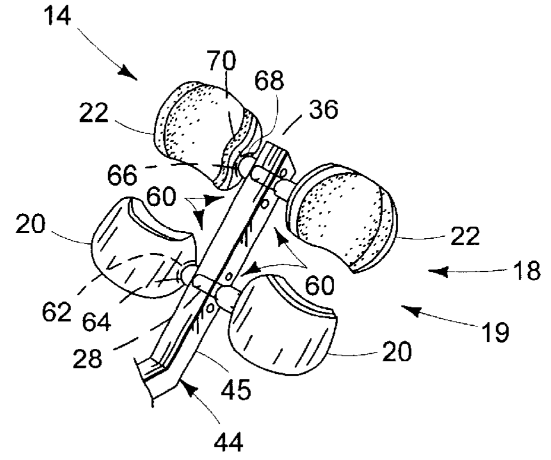
FIG. 3 is a fragmentary perspective view showing the lower-extremity engagement structure of FIG. 1 with other suitable stirrup assemblies.

It is within the scope of the invention that other suitable mechanisms may be used to rotatably couple the stirrups to structure 14. For example, instead of having the stirrups rotate with the respective axles, each stirrup instead may be rotatably mounted on the respective axle, such as with bearings or other suitable rotatable mounts. A benefit of such a construction is that the stirrups on each end of an axle may be rotated independent from each other. This may be desirable, for example, when a user prefers to insert or remove one lower extremity at a time and/or when a user's lower extremities are not of equal size. An example of such a construction is shown in FIG. 3. As shown, each stirrup 20 and 22 includes a bearing assembly 60 that enables the stirrup to rotate about its corresponding axle. Bearing assembly 60 may include any suitable structure that permits rotation of the stirrup relative to the axle. Illustrative examples of suitable structures for bearing assembly 60 are shown in FIG. 3. Heel-engaging stirrups 20 demonstrate an example of a bearing assembly 60 that includes a plurality of ball-bearings 62 that travel within races 64 as the stirrup is rotated. Foot-engaging stirrups 22 demonstrate another example of a suitable bearing assembly, namely, a bearing assembly 60 in which axle 36 includes a neck 66 that is received through a bore 68 in stirrup 22 and a head 70 that is larger in cross-sectional area than bore 68. As shown, head 70 is retained within the stirrup to provide a rotational mount for the stirrup upon the axle.

Figure 4:
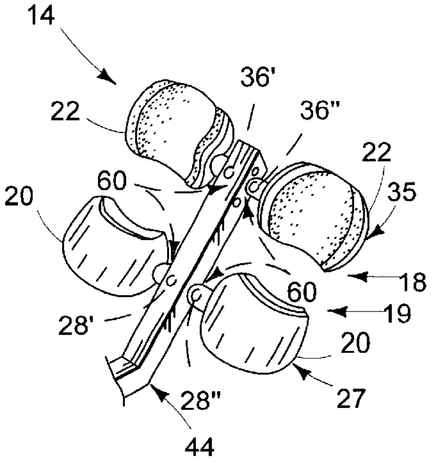
FIG. 4 is a fragmentary perspective view showing the lower-extremity engagement structure of FIG. 1 with other suitable stirrup assemblies.

As another example of a suitable mounting mechanism for the stirrups, each stirrup may be mounted on its own axle. This configuration enables each stirrup to be rotatably and/or adjustably positioned independent of the other stirrups. An example of such a construction is shown in FIG. 4, in which the heel-engaging stirrups are mounted on axles 28' and 28" and the foot-engaging stirrups are mounted on axles 36' and 36". To further demonstrate that a variety of rotatable configurations may be used for the independent axles, heel-engaging stirrups 20 are illustratively presented with axles 28' and 28" that are nonrotatably mounted on the stirrups and which are rotatably coupled to frame portion 44 by any suitable bearing assembly 60 so that the axles and stirrups rotate as a unit. As another example, foot-engaging stirrups 22 are illustratively presented with axles 36' and 36" that nonrotably extend from frame portion 44 and which are rotatably coupled to the stirrups. It is also within the scope of the invention that the stirrups may be fixedly, or non-rotatably, mounted relative to structure 14.

It should be understood that the examples of suitable stirrups and mounting mechanisms therefor may be used with any devices according to the present invention. Typically, each of the stirrups will utilize the same type of mount, but it is also within the scope of the invention that the stirrup assemblies, or more commonly the stirrup pairs, may utilize different mounting mechanisms. For example, one of the stirrup pairs, such as pair 27, may be non-adjustably mounted relative to the frame portion, with the other stirrup pair, such as pair 35, being adjustably mounted relative to the frame portion and the other stirrup pair to provide for selectively sizing of the distance between the stirrup pairs. An example of this configuration is graphically illustrated in FIG. 4, although it is also within the scope of the invention that the bearing assembly of FIG. 4 may be implemented with other stirrups and that other stirrup pairs may have the adjustability shown in FIG. 4.

Figure 5:
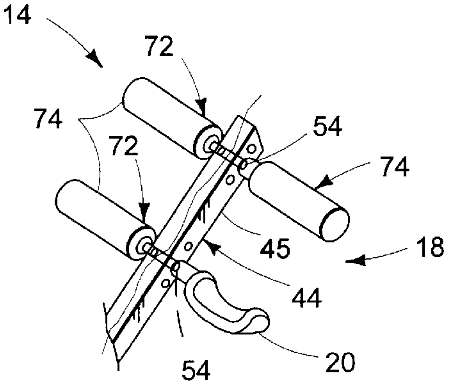
FIG. 5 is a fragmentary perspective view showing other embodiments of the lower-extremity engagement structure of the device of FIG. 1.

Although the stirrups described above provide examples of suitable leg-engagement structures for use with devices 10 according to the present invention, other such structures may also be used and are within the scope of the invention. For example, and as shown in FIG. 5, structure 14 may include mounts 18 that include at least one post or other tubular member 72 that projects from frame portion 44 and which is adapted to support a user's feet and/or the lower portions of a user's legs. Preferably, member 72 includes an outer layer 74 formed from a soft or padded material to cushion the engagement with the user's body. It is within the scope of the invention that member 72 may be constructed with any of the adjustability and/or rotatability described and/or illustrated above with respect to stirrups 20 and 22. In the left side of FIG. 5, mount 18 includes a pair of spaced-apart tubular members 72, with one member being adapted to receive and support an upper portion of a user's foot and the other member being adapted to receive a support a heel or lower-leg portion of the user's lower extremity. On the right side of FIG. 5, mount 18 includes a tubular member 72 and a heel-engaging stirrup 20 to graphically illustrate that the lower-extremity engagement structure may have a variety of configurations, such as including selected ones of the mounts, and variations thereto, described and/or illustrated herein.

Figure 6:
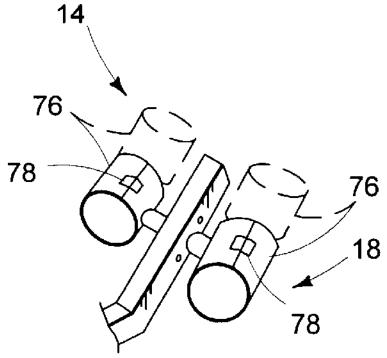
FIG. 6 is a fragmentary perspective view showing other embodiments of the lower-extremity engagement structure of the device of FIG. 1.
Figure 7:
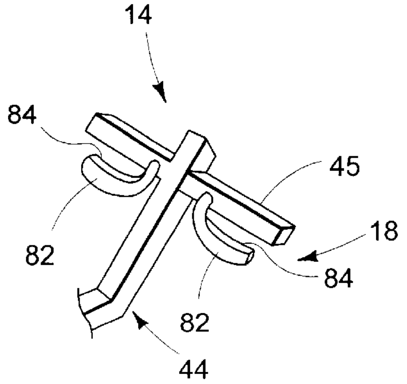
FIG. 7 is a fragmentary perspective view showing other embodiments of the lower-extremity engagement structure of the device of FIG. 1.
Figure 8:
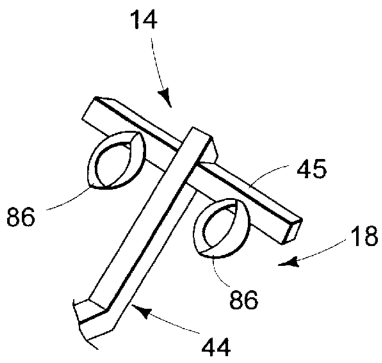
FIG. 8 is a fragmentary perspective view showing other embodiments of the lower-extremity engagement structure of the device of FIG. 1.

It is also within the scope of the invention that lower-extremity engagement structure 14 does not include a pair of spaced-apart mounts 18 for each lower extremity. Instead, structure 14 may include a single mount for each of the user's lower extremities. For example, structure 14 may include leg cuffs 76 instead of the stirrup assemblies. An example of such a configuration is shown in FIG. 6, in which it can be seen that cuffs 76 are adapted to releasably extend around the user's lower leg, as shown in solid lines, and/or feet, as shown in dashed lines. Cuffs 76 may be formed from an elastomeric material that stretches to permit a user's lower extremities to pass therethrough. Alternatively or additionally, the cuffs may include a fastening mechanism 78, such as buckles, straps, hook-and-loop closure mechanisms, ties, or the like that permit a normally open cuff to be secured around a user's lower extremity. As another example, region 45 of frame portion 44 may extend generally transverse to the long axis of body 12, such as shown in FIG. 7. In FIG. 7, another example of a suitable mount 18 is also shown, namely a rigid brace 82 that extends from region 45 and around which a user's feet are extended, and optionally cushioned by padding 84. As discussed, this configuration requires a user to resist the user-applied tractive forces with the user's feet. As a result, this configuration may not be as desirable for some applications when compared to mounts 18 in which the user is not required to exert this positive retaining force by flexing the user's feet while device 10 is used. Still another example is shown in FIG. 8, in which flexible straps or loops, 86 are used to support the user's lower extremities.

Figure 10:
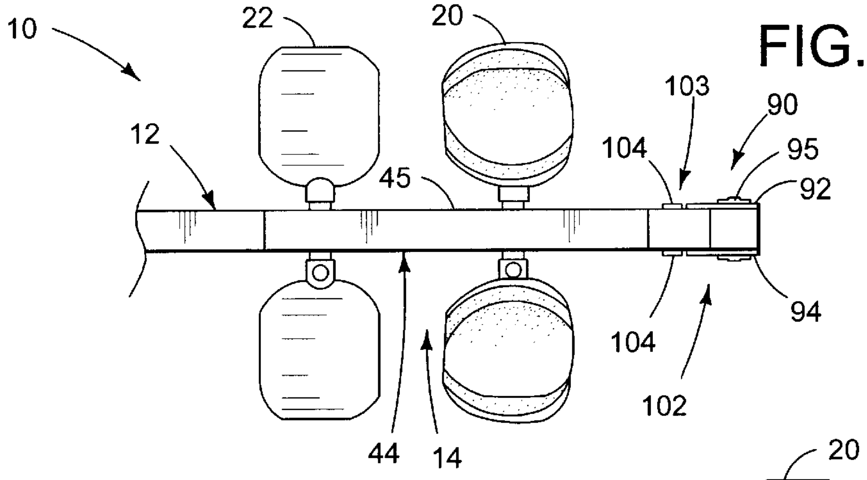
FIG. 10 is a fragmentary top plan view of the device of FIG. 1, with both the lower-extremity engagement structure in a stowed configuration.
Figure 9:
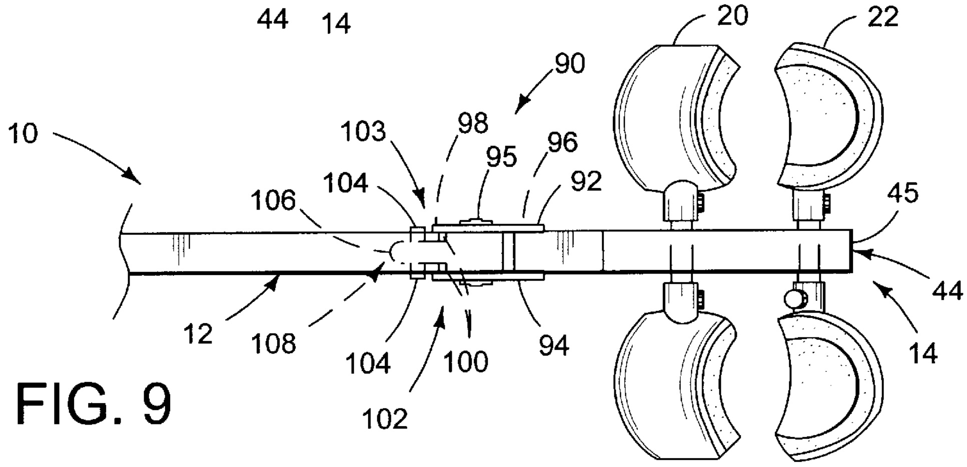
FIG. 9 is a fragmentary top plan view of the device of FIG. 1, with the lower-extremity engagement structure in an extended configuration.

Returning to FIG. 1, it can be seen that structure 14 is pivotally coupled to body 12 by a hinge assembly 90. Hinge assembly 90 enables structure 14 to be selectively pivoted between an operative, or extended, configuration, which is shown in FIGS. 1 and 9, and a stowed configuration, which is shown in FIG. 10. As shown in FIG. 10, structure 14 may be pivoted about hinge assembly 90 to a position in which it is at least substantially overlapping with a body 12. Examples of situations in which it would be desirable to collapse structure 14 to its stowed configuration include storage and/or transport of the device where it may be desirable for the device to have a shorter overall length and/or overall height.

Hinge assembly 90 may include any suitable structure for pivotally coupling body 12 and lower-extremity engagement structure 14 together for pivotal movement of structure 14 between the extended and stowed configurations. An example of a suitable configuration for hinge assembly 90 is shown in FIGS. 1 and 9–10. As shown, hinge assembly 90 includes a pair of hinge plates 92 and 94. As perhaps best seen in FIG. 1, plates 92 and 94 extend from structure 14 and are pivotal about an axis defined by axle 95, which pivotally interconnects body 12 and lower-extremity engagement structure 14. It should be understood that at least one of hinge plates 92 and 94 may alternatively extend from body 12 instead of structure 14.

As shown in FIG. 1, each hinge plate includes bores 96 and 98 into which pins 100 may be received to releasably retain structure 14 in a selected configuration. In the illustrated embodiment, the hinge plates include a first bore 96, which retains structure 14 in its stowed configuration when pins 100 are inserted therethrough, and a second bore 98, which retains structure 14 in its extended configuration when pins 100 are inserted therethrough. The pin and bore assembly described above may be referred to a lock mechanism 102. As also shown in FIGS. 1 and 9–10, lock mechanism 102 includes a release mechanism 103 that is adapted to withdraw pins 100 from the bores responsive to a user depressing or otherwise actuating buttons 104. As perhaps best seen in FIG. 9, buttons 104 are coupled via a leaf spring 106 to pins 100 such that when the buttons are depressed, the pins are withdrawn from a position in which they would pass through one of the bores. Leaf spring 106 provides an example of a suitable biasing mechanism 108 that urges the pins to automatically extend to a position in which the pins pass through the bores to retain structure 14 in a selected configuration. As such, the device may be described as having a hinge assembly with an automatic lock mechanism. It is within the scope of the invention that other suitable biasing mechanisms 108 may be used, such as coil springs, resilient (compressible or extendable) members, and the like. Similarly, release mechanism 103 may utilize other suitable forms of actuators other than buttons 104, such as levers, slides, pull tabs, and the like. It is also within the scope of the invention that hinge assembly 90 does not include a lock mechanism and/or a biasing mechanism.

Figure 11:
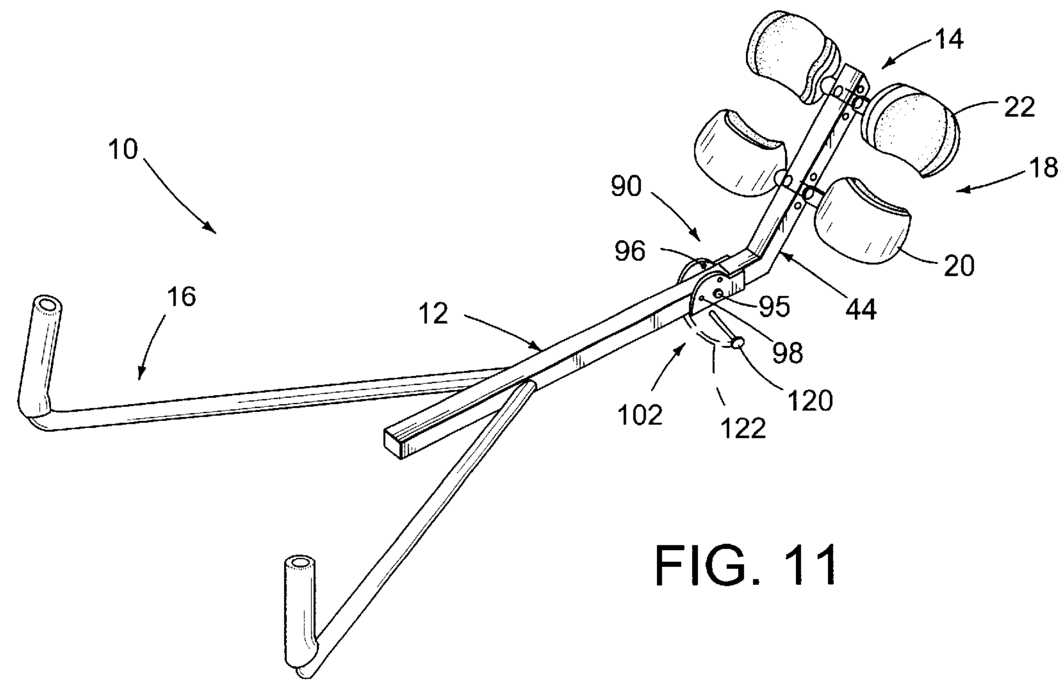
FIG. 11 is a perspective view of another isometric exercise device constructed according to the present invention.

Another example of a suitable hinge assembly 90 is shown in FIG. 11. As shown, lock mechanism 102 includes a removable pin 120, which may be either free from device 10 or tethered thereto by a leash 122. The structure shown in FIG. 11 provides a simpler structure than the previously described automatically engaging lock mechanism. In the illustrated embodiment, structure 14 is pivoted relative to body 12 until the bores through the hinge plates and corresponding portion of body 12 (or structure 14) are aligned, and then pin 120 is inserted through the body. To release the lock assembly, the user simply pulls the pin out of the bore.

Figure 24:
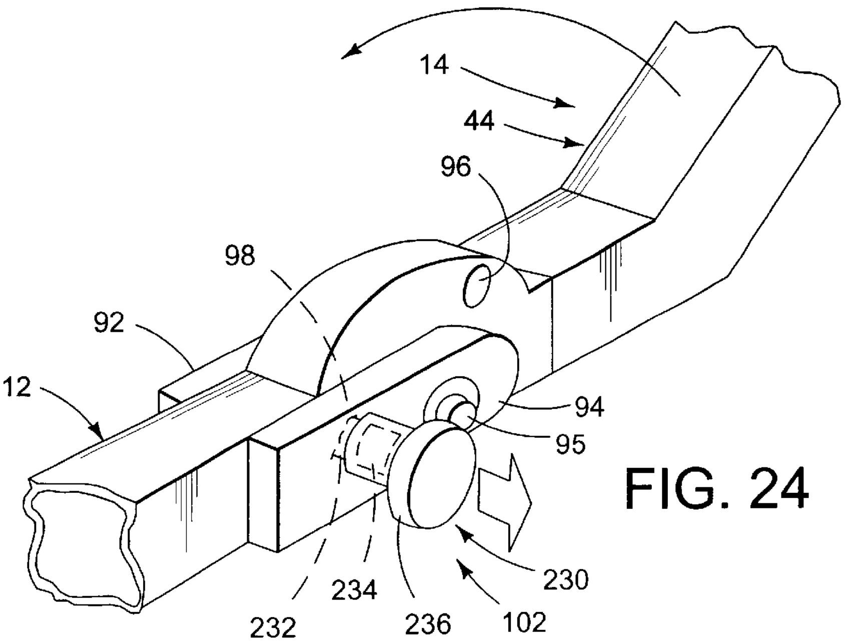
FIG. 24 is a fragmentary perspective view of another suitable lock mechanism for use in embodiments of the device that include a pivotal lower-extremity engagement structure.

Another example of a suitable lock mechanism 102 is shown in FIG. 24, in which the lock mechanism includes what may be referred to as a captive pin 230. More specifically, the lock mechanism includes a pin 232 that is biased, such as by a spring or other suitable biasing mechanism 234 into a position where it will extend into bores 96 or 98 from external body 12. Captive pin 230 also includes a head, or knob, 236 that a user grasps and draws against the biasing force in a direction generally transverse to the long axis of body 12 to release the lock mechanism so that the lower-extremity engagement structure may be pivoted relative to the body. When a user releases the knob, the biasing mechanism automatically urges the pin to a position where it will insert into one of bores 96 or 98, subject to the bore being properly aligned to receive the pin. Yet another example of a captive pin 230 is a cam mechanism that selectively draws the pin into and out of bores 96 or 98 as the cam is rotated relative to the body.

Figure 12:
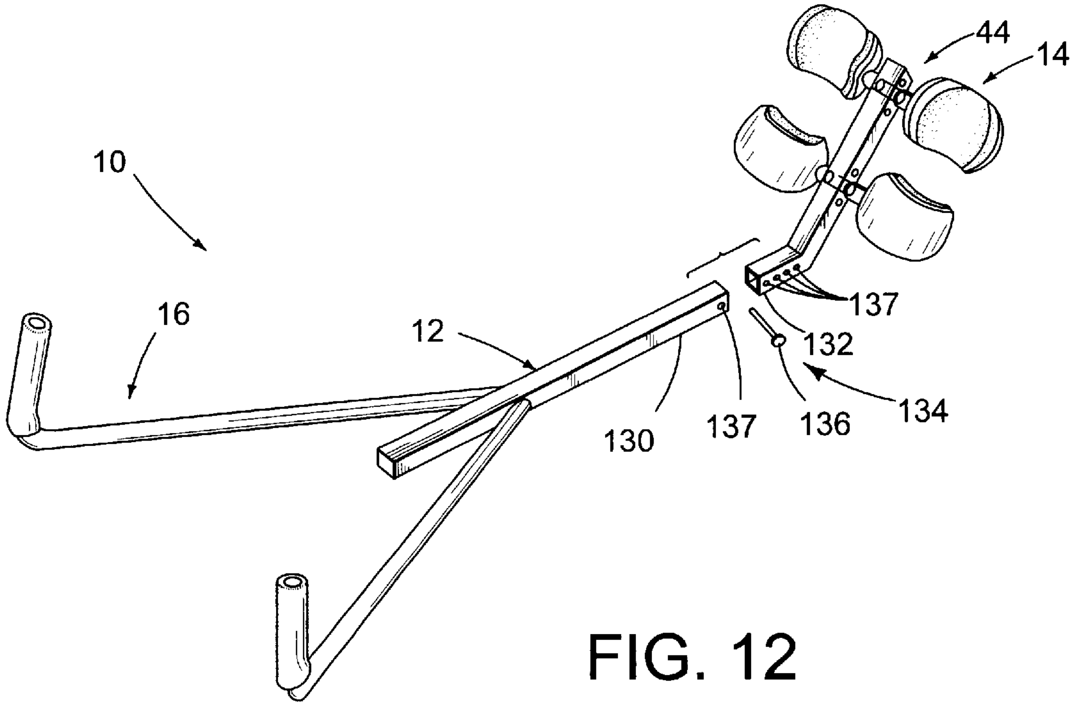
FIG. 12 is a perspective view of another isometric exercise device constructed according to the present invention.

It is also within the scope of the invention that structure 14 is removably coupled to body 12, but not pivotally coupled to the body. An example of such a configuration is shown in FIG. 12. As shown, body 12 terminates at an end region 130 to which a corresponding end region 132 of structure 14 is releasably coupled by a fastening mechanism 134. In the illustrated embodiment, the end regions are telescopingly coupled together and are retained in an assembled configuration by a pin 136 that passes through a bore 137 in the end regions. As shown, end region 132 of structure 14 is received within end region 130 of body 12, but it is within the scope of the invention that this relationship may be reversed. Similarly, in FIG. 12, a plurality of bores 137 are shown in end region 132 to illustrate that the regions may optionally be adjustably secured together, such as to extend the overall length of device 10. It is within the scope of the invention that at least one of the end regions may include more than one bore to permit the length of the device to be adjusted and that other suitable fastening mechanisms may be used. Examples of other suitable fastening mechanisms include spring-biased pins, such as described above with respect to pins 100 (including the variants described above), mating threads on the respective end regions, and other twist-to-lock mechanisms.

Figure 13:
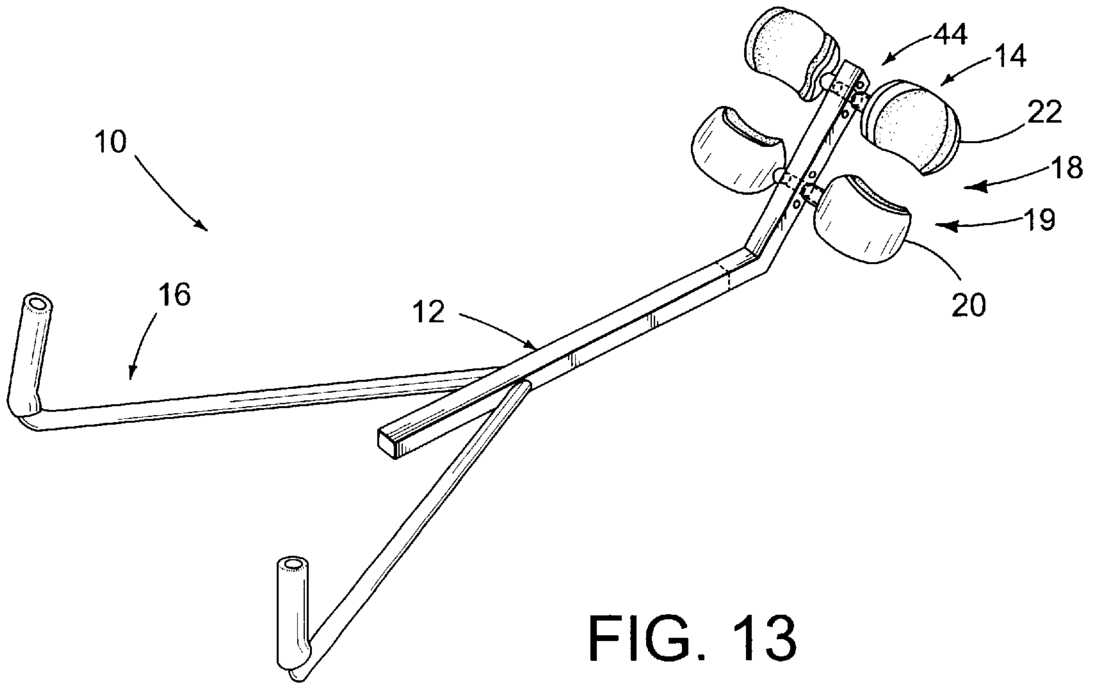
FIG. 13 is a perspective view of another isometric exercise device constructed according to the present invention.

In a further variant, it is within the scope of the invention that the lower-extremity engagement structure is fixedly coupled to body 12. By "fixedly coupled," it is meant that structure 14 is not adapted to be removed and replaced from engagement with body 12 without destroying at least a portion of body 12, structure 14, or any intervening structure. Examples of configurations in which body 12 and structure 14 are fixedly coupled together include embodiments in which the portions are integrally formed with each other (as shown in solid lines in FIG. 13, and embodiments in which the portions are welded or adhesively bonded together, as shown in dashed lines in FIG. 13. Alternatively, "releasably coupled" portions and "removably coupled" portions refer to portions that are configured to be repeatedly coupled together into an operative position, disconnected, and then recoupled together without disassembly or destruction of the portions.

A benefit of fixedly coupling body 12 and structure 14 together is that structure 14 may be integrally formed with body 12, or if separately formed from body 12, secured thereto with less complex and/or expensive structure as may be required for a pivotal or releasable coupling. A benefit of a removable coupling is that structure 14 can be removed from body 12, such as for storage or transportation, thereby reducing the overall dimensions of the device. A removable lower-extremity engagement structure also permits the selective removal and replacement of structure 14, such as if necessary due to wear. It also permits the interchange of structure 14 with a different type of lower-extremity engagement structure or even a lower-extremity exercising structure, which is configured for use by a user during exercises or strengthening activities. Regardless of the interconnection of structure 14 with body 12, any of these embodiments of device 10 may include any of the mounts 18 and/or transmitting portions 16 described and/or illustrated herein.

As discussed, device 10 enables the magnitude and rate of application of the tractive forces to be applied and selected by a user. As such, device 10 may be described as being configured to permit the application of user-generated tractive forces, meaning that the user controls at least the timing and magnitude of the tractive forces, and commonly, the application and release of these forces while device 10 is being used. In contrast, many conventional devices either automatically apply a predetermined and constant tractive force as the device is used, or only permit the magnitude of the tractive force to be adjusted while device 10 is not being used.

Returning to FIG. 1, it can be seen that a transmitting portion 16 includes a pair of handle assemblies 150 that extend from body 12. Each handle assembly includes a gripping portion 152, which is positioned and adapted to be gripping by a user of device 10, and a force-transmitting structure 154, which interconnects the handle with body 12 so that user-applied tractive forces are transmitted from grippable portion 152 to body 12 and therefore to lower extremity engagement structure 14. In the illustrated embodiment, it can be seen that the handle assemblies extend at divergent angles from body 12, generally away from structure 14. In this position, the gripping portions are positioned to be grasped by a user's hands when the hands are at the user's sides. As such, device 10 has a generally Y-shaped configuration in FIG. 1. In FIG. 1, gripping portions 152 extend generally transverse to the long axis 47 of body 12 and out of a plane defined by body 12 and structure 154. It is within the scope of the invention that portions 152 may extend in other directions, such as transverse to long axis 47 and generally within this plane, as indicated in dashed lines in FIG. 1.

Figure 14:
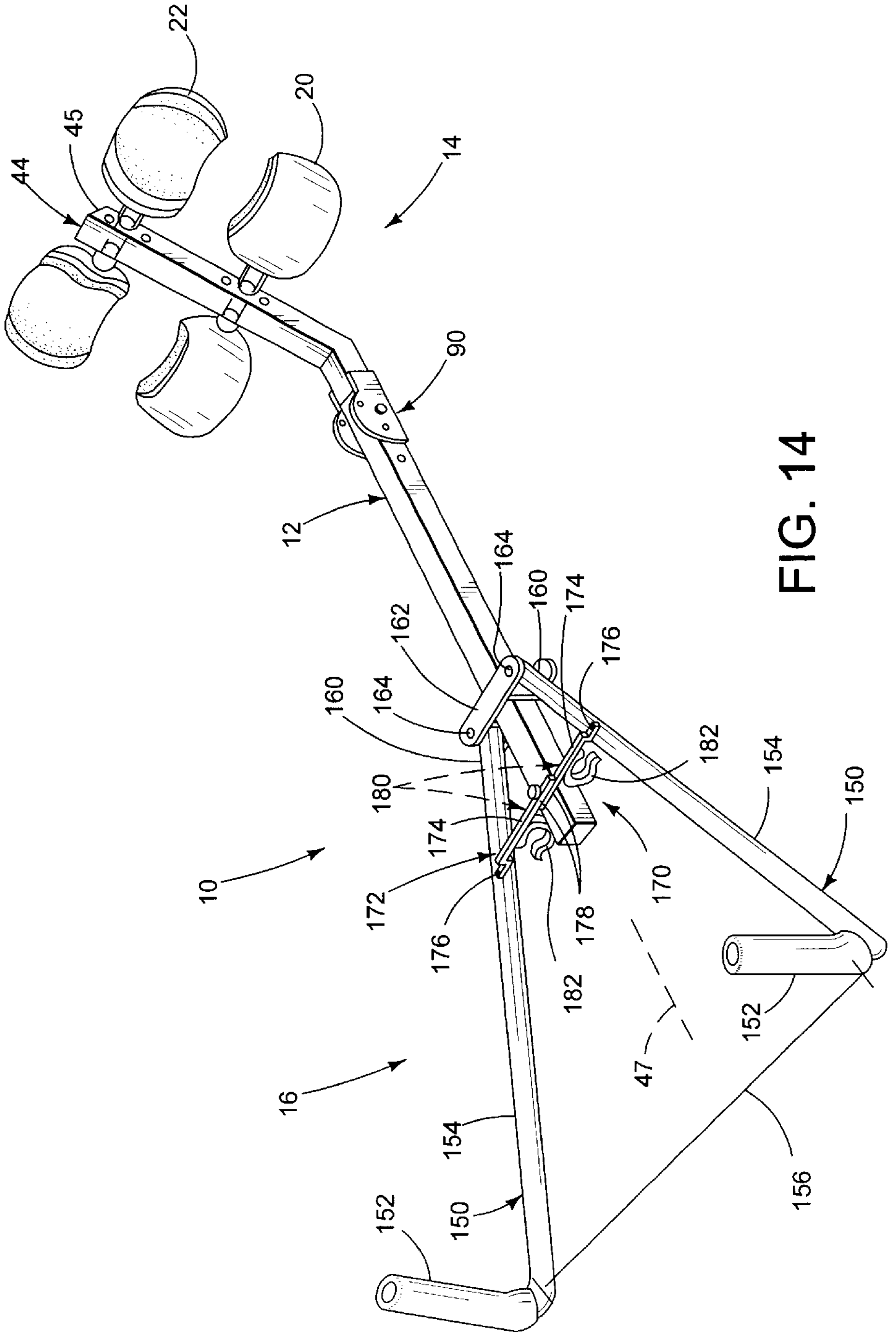
FIG. 14 is a perspective view of another isometric exercise device according to the present invention.

Because device 10 may be used by a variety of users having different sizes, the distance 156 between handle assemblies 150 is preferably (but not required to be) adjustable. An example of an embodiment of device 10 in which the distance between handle assemblies 150 is adjustable is shown in FIG. 14. As shown, each handle assembly 150 includes an end region 160 distal gripping portion 152 that is pivotally coupled by body 12. In the illustrated embodiment, end regions 160 are pivotally coupled to body 12 by a bracket 162, which includes pins 164 that extend through regions 160 and define pivot axes therefor. It is within the scope of the invention that any other suitable mount that enables pivotal movement of the handle assemblies relative to body 12 may be used.

Also shown in FIG. 14 is a handle retention structure 170 that is adapted to limit the extent to which the handle assemblies may pivot away from each other, thereby limiting the maximum distance 156 between the handle assemblies. Retention structure 170 includes a leash assembly 172 that is coupled to each structure 154 and limits the extent to which the handle assemblies may be pivoted away from the long axis of body 12.

In the illustrated embodiment, leash assembly 172 includes a pair of leashes 174, with each leash 174 including end regions 176 and 178 that are respectively coupled to structures 154 and body 12. A benefit of each handle assembly being tethered to body 12 by its own leash 174 is that the handles may be independently positioned relative to each other, within the range of positions defined by the respective leash 174. It is within the scope of the invention, however, that leash assembly 172 may couple the handle assemblies together, such that the maximum distance between the assemblies is limited, but the distance between each handle assembly and axis 47 is not required to be equal. Leashes 174 may be constructed from a variety of materials, including flexible and/or rigid materials. Examples of rigid materials include pivotally and/or slidably coupled metal or rigid plastic members. Examples of flexible materials include ropes, cords, straps, and extruded or molded flexible plastic materials. Leashes 174 may also be formed from a plurality of adjustably interconnected rigid materials, such as chain, hinged metal or rigid plastic segments, and rigid telescoping members. In some embodiments, it may be desirable for the retention structure to include a biasing mechanism 180 that urges the handle assemblies toward each other and/or toward long axis 47. Examples of suitable biasing mechanisms include springs and elastomeric bands, such as may be used to form leashes 174.

Figure 15:
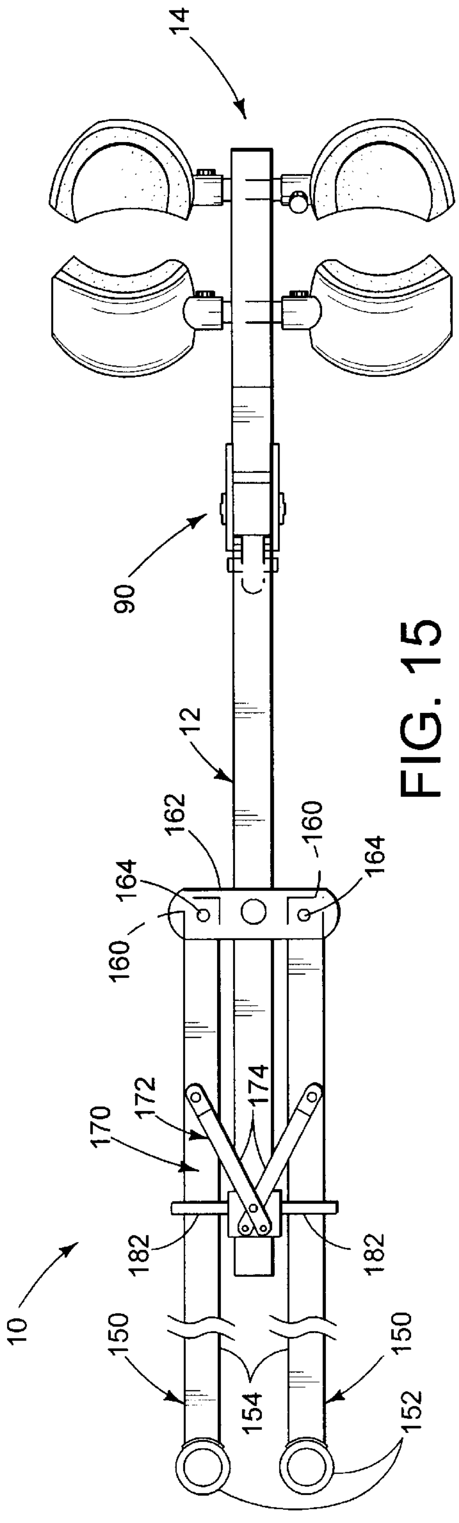
FIG. 15 is a top plan view of the device of FIG. 14, with the transmitting portion pivoted to a collapsed configuration.
Figure 16:
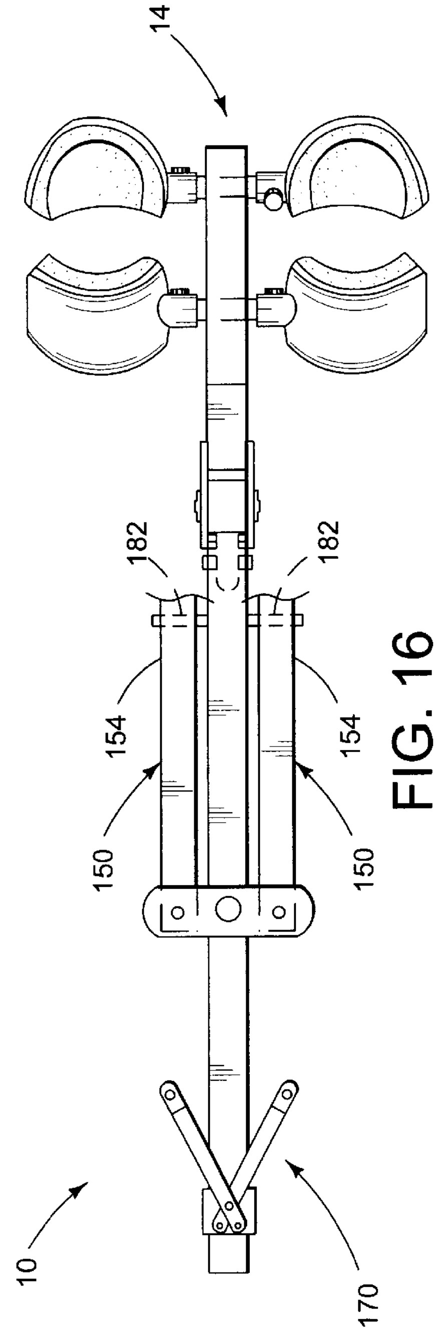
FIG. 16 is a top plan view of the device of FIG. 14, with the transmitting portion pivoted to another collapsed configuration.

As discussed, pivotally coupling handle assemblies 150 to body 12 enables the distance 156 between the handle assemblies to be selectively adjusted by a user. One possible application of this adjustment mechanism is discussed above, namely to size device 10 for use by users with different girths and/or preferred operative configurations for device 10. Another possible application is to permit the handle assemblies to be pivoted from the extended, or operative, configuration shown in FIG. 14 to a stowed configuration, such as shown in FIGS. 15 and 16. As shown, the handle assemblies are pivoted to configurations in which they extend generally parallel to axis 47 and therefore reduce the overall width of device 10. In FIG. 15, the handles are pivoted toward each other and away from structure 14, while in FIG. 16, the handles are pivoted toward structure 14 to provide more compact overall shape for device 10. It should be understood that embodiments of device 10 that are intended to be pivoted to the stowed configuration shown in FIG. 16 should either be formed without a retention structure 170, include a leash assembly that is sufficiently elastomeric or stretchable to permit the pivotal range required to pivot the handle assemblies to the configuration shown in FIG. 16, where they are releasably retained by retainers 182, or the device should include a releasable retention structure (such as a releasable leash assembly), in which the at least one of the body and/or the handle assemblies may be selectively disconnected by the retention structure. In the illustrated embodiment, leash assembly 170 is shown disconnected from structures 154 to permit the handle assemblies to pivot to the illustrated position. Also shown in FIGS. 15–16 are retainers 182 that releasably engage the handle assemblies to retain the handle assemblies in the stowed configuration.

As discussed above, it is within the scope of the invention that the position of mounts 18 relative to body 12 may be adjustable, such as to permit device 10 to be sized for use by a variety of differently sized individuals. As such, it is not necessary for the distance between transmitting portion 16 and body 12, such as the distance between grippable portions 152 and body 12, to be adjustable. However, in some embodiments, it may be desirable for this distance to be adjustable.

Figure 17:
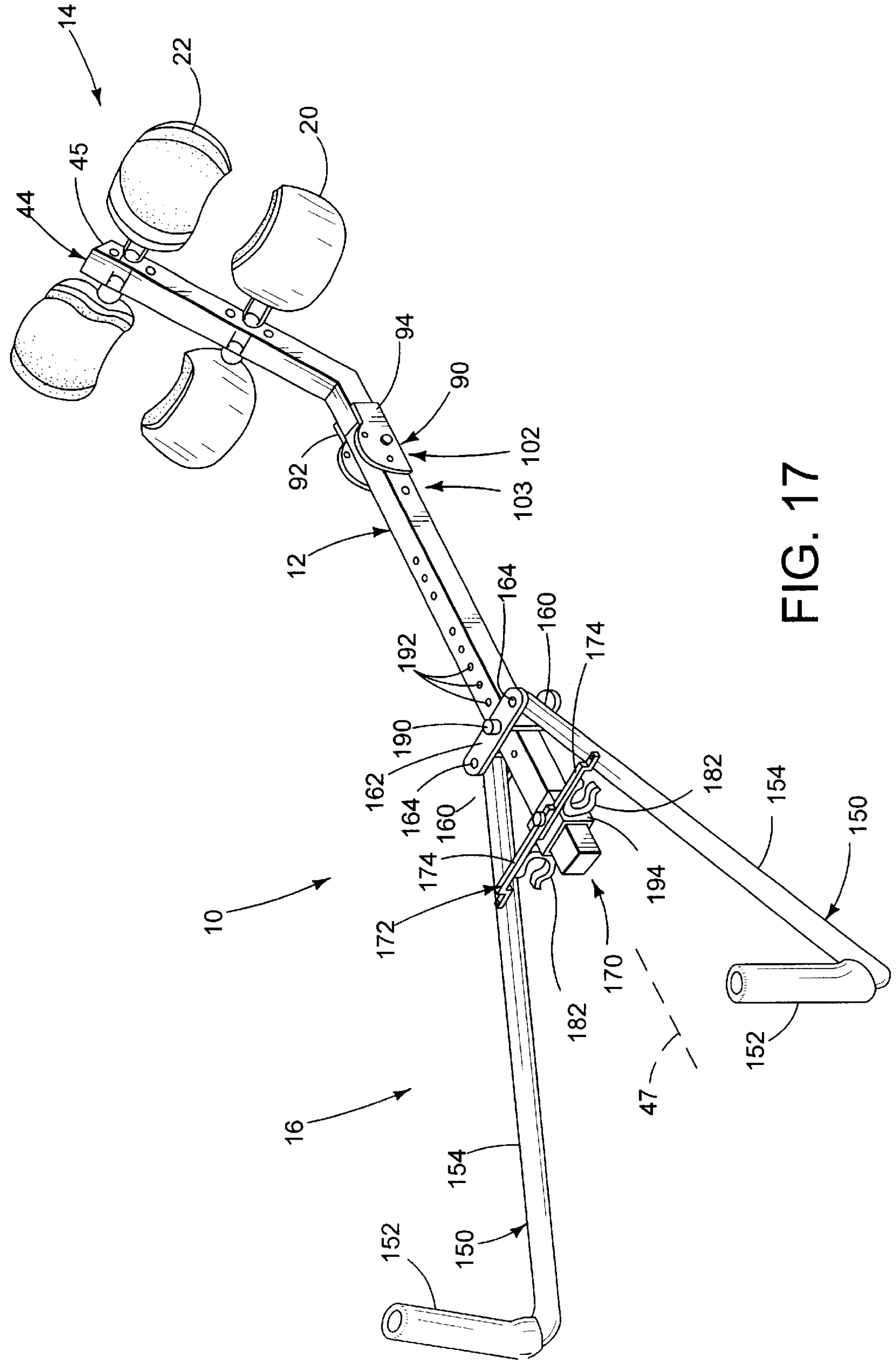
FIG. 17 is a perspective view of another isometric exercise device according to the present invention.
Figure 19:
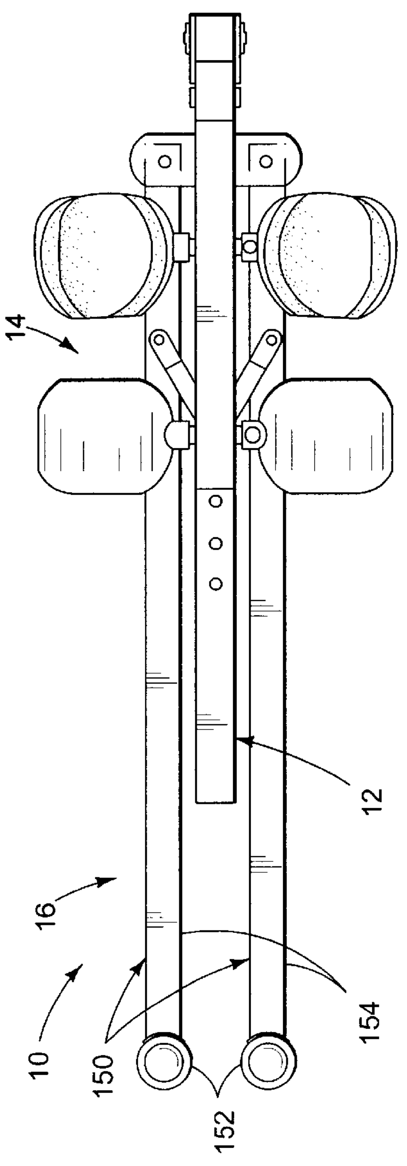
FIG. 19 is a top plan view of the device of FIG. 17, with both the transmitting portion and the lower-extremity engagement structure in collapsed configurations.
Figure 18:
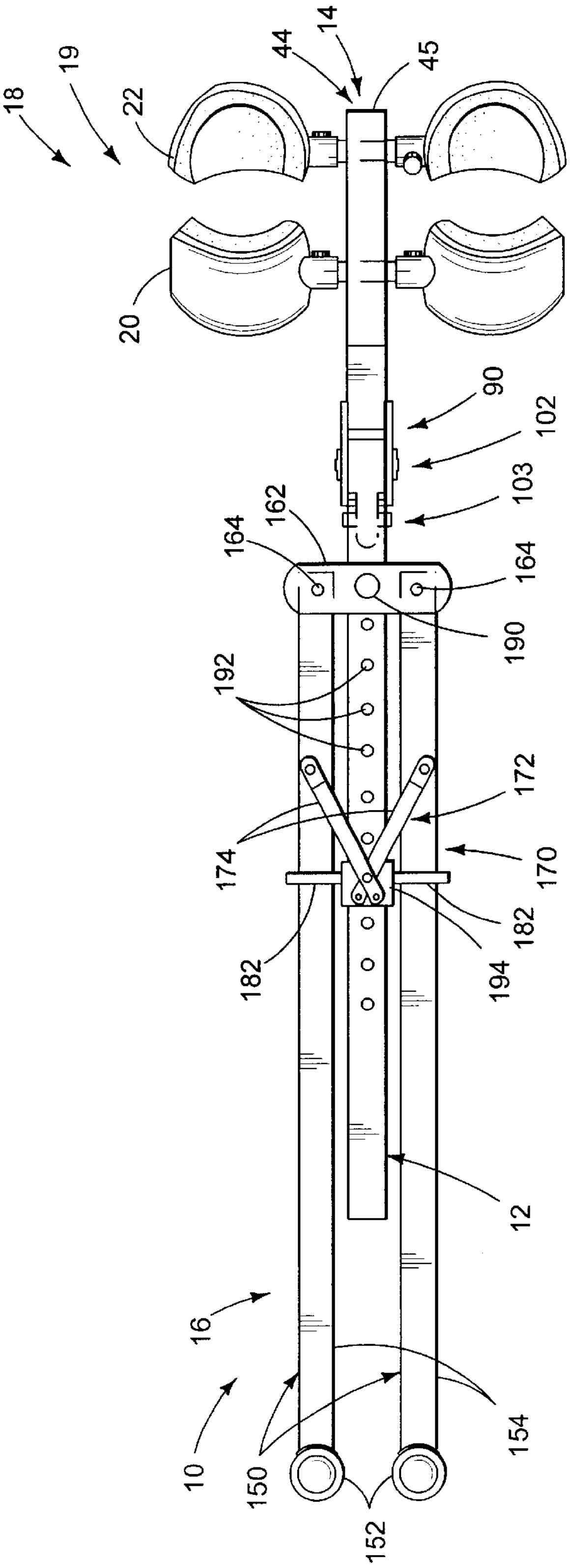
FIG. 18 is a top plan view of the device of FIG. 17, with the transmitting portion in a stowed configuration and the lower-extremity engagement structure in an extended configuration.
Figure 20:
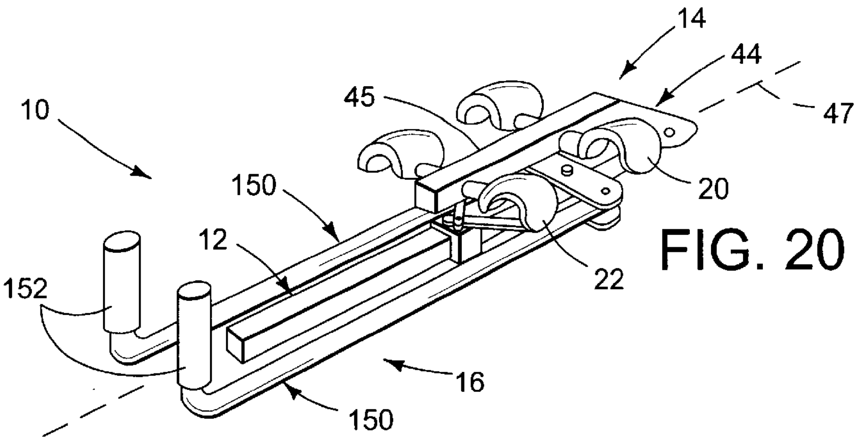
FIG. 20 is a perspective view of the device of FIG. 17, with both the transmitting portion and the lower-extremity engagement structure in collapsed configurations.

An example of a device 10 according to the present invention in which transmitting portion 16 is adjustably mounted on body 12 is shown in FIG. 17. As shown, transmitting portion 16, including handle assemblies 150, bracket 162, and retention structure 170 are adjustably positioned along the length of body 12. In the illustrated embodiment, bracket 162 is slidably adjustable along the length of body 12 and includes a fastener 190 that selectively engages a plurality of bores, or detents, 192, along body 12 to secure the transmitting portion in a selected position along the body. In dashed lines in FIG. 17, selected mounting positions for transmitting portion 16 are shown for the purpose of illustration. Fastener 190 may be freely insertable and removable from bracket 162, or alternatively may be spring biased into a locked position, in which the fastener is positioned to engage one of the detents. As also shown in FIG. 17, retention structure 170, namely leashes 174 are mounted on a carriage 194 that also slides along body 12 responsive to repositioning of bracket 162 along the body. Similar to several of the previously described embodiments of device 10, the embodiment shown in FIG. 17 may also be selectively collapsed from the extended, or operative, configuration shown in FIG. 17 to a collapsed, or stowed, configuration, which is shown in FIGS. 18–20. As shown, the overall length of the device may typically be further collapsed from the configurations illustrated previously when transmitting portion 16 is adjustably mounted on body 12.

Although the embodiment of device 10 shown in FIG. 17 includes not only an adjustable transmitting portion 16 but also an adjustable lower-extremity engagement structure 14, it is within the scope of the invention that the adjustable transmitting portion may be implemented with any of the lower-extremity engagement structures described and/or illustrated herein. Similarly, device 10 may be implemented with an adjustable transmitting portion that does not include a retention structure 170 or pivotal handle assemblies 150.

Figure 21:
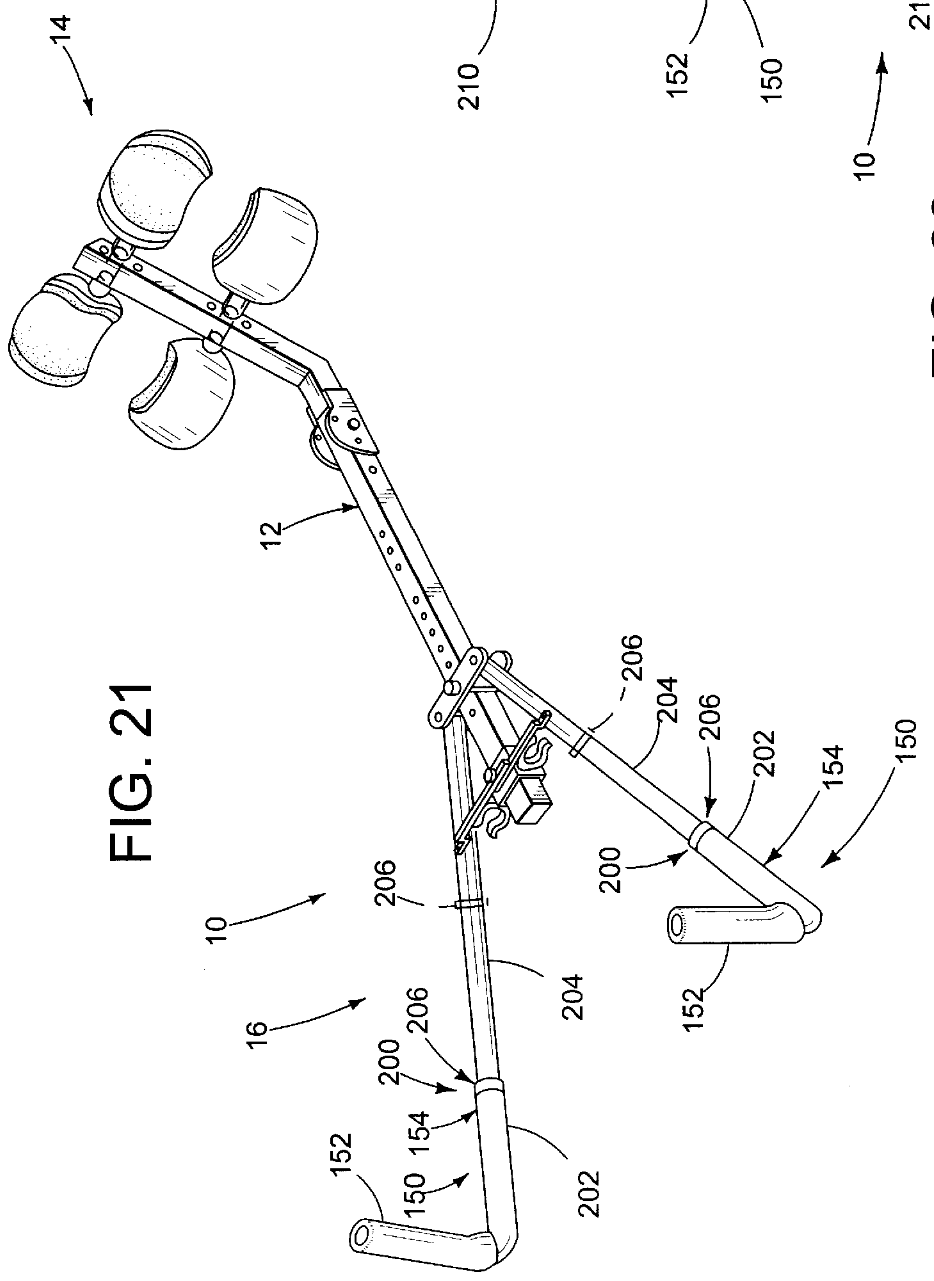
FIG. 21 is a perspective view of another isometric exercise device according to the present invention.

Another suitable mechanism for providing adjustability to the size of device 10 when it is in its operative, or extended, configuration is for the length of handle assemblies 150 to be adjustable. An example of such a device is shown in FIG. 21, in which the length of transmitting structure 154 is selectively adjustable by an adjustment mechanism 200. Although illustrated in combination with an adjustable bracket 162 that may be selectively positioned along the length of body 12, it is also within the scope of the invention that handle assemblies 150 with adjustable lengths may be used with embodiments of device 10 that do not include an adjustable bracket 162. Mechanism 200 may include any suitable structure that enables the length of transmitting structure 154 to be adjusted.

An example of a suitable configuration for an adjustable transmitting structure 154 is shown in FIG. 21, in which structure 154 includes telescoping members 202 and 204 that are slidably adjustable relative to each other, and mechanism 200 includes a releasable fastener 206 that is schematically illustrated in FIG. 21 and selectively secures the members in a selected position relative to each other. For example, the members may be releasably retained in a selected length by an internal cam structure, by spring biased pins that extend through apertures in the outer member, and/or by a pin that is selectively inserted through selected ones of aligned bores in the members. As also indicated graphically in dashed lines in FIG. 21, it is within the scope of the invention that structure 154 includes more then two telescoping members and corresponding fasteners 206. Similarly, the length of structure 154 may be adjustable by mechanisms other than telescoping members, such as by including two or more members that are selectively secured in a side-by-side relationship to define the length of structure 154.

Figure 22:
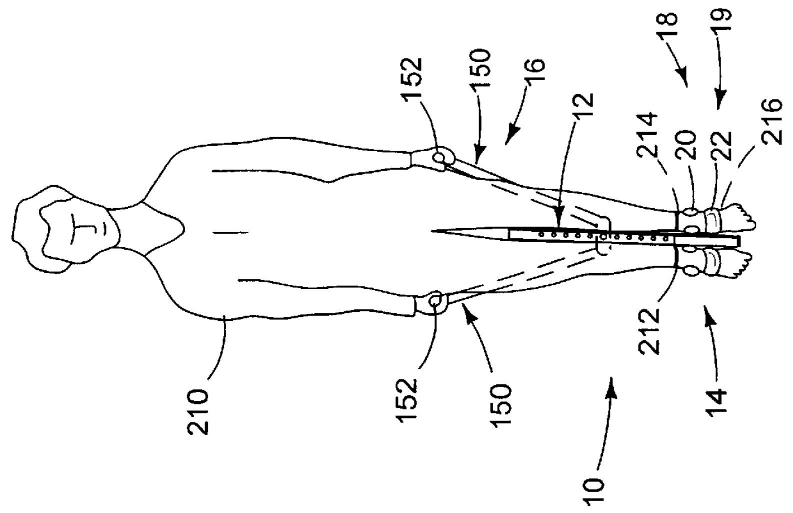
FIG. 22 is a top view illustrating the device of FIG. 17 being used.

In FIG. 22, device 10, such as the embodiment shown in FIG. 17, is shown being used by a user 210. As shown, the user's lower extremities 212 are received and supported, or retained, by lower-extremity engagement structure 14. In the illustrated embodiment, the back of the user's heel region 214 of each extremity is supported by a heel-engaging stirrup 20, and the front, or top, of each of the user's feet 216 is supported by a foot-engaging stirrup 22. When the user grasps grippable portions 152 of handle assemblies 150 and applies a force thereto that is directed generally toward the user's lower extremities, a tractive force is applied to the user's spine and lower back. The timing and the magnitude of the tractive force is controlled by the user while the device is being used, namely, by the user selecting when and how hard to apply this user-exerted force. As such, while device 10 is being used, the user may experience natural feedback as the tractive forces are applied to the user's body, and then discontinue, continue or adjust the application of the tractive forces without repositioning or removing the user's hands or lower-extremities, and even without interrupting the application of the tractive forces. Similarly, because the device enables a user to apply the user-exerted forces with differing magnitudes to each gripping portion 152, the user may selectively apply a localized tractive force that is stronger on one side of the user's back than the other. As an extension of this application, the user may even only apply force to one of the grippable portions at a time.

INDUSTRIAL APPLICABILITY

Exercise devices according to the present invention are applicable to the fitness, rehabilitation, health and other industries in which is it necessary or desirable to apply tractive forces to a user's lower back or other body portions.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

I claim:

1. An isometric exercise device, comprising:

a body;

a lower extremity engagement structure associated with the body and adapted to engage and retain a user's lower extremities, wherein the engagement structure includes a frame portion and, for each of the user's lower extremities, a pair of mounts that are coupled to the frame portion;

a transmitting portion associated with the body generally distal the lower extremity engagement structure, wherein the transmitting portion includes a pair of handle assemblies with grippable portions that are adapted to be grasped by a user's hands while the user's lower extremities are engaged by the lower extremity engagement structure such that when a user exerts a user-directed force upon the grippable portions in a direction generally toward the lower extremity engagement structure, a tractive force is applied to the user's back; and a hinge assembly pivotally coupling the frame portion to the body for pivotal movement of the frame portion and the pairs of mounts as a unit relative to the body in a range of configurations that include an extended configuration, in which the engagement structure extends generally away from the body and the transmitting portion relative to the hinge assembly, and a collapsed configuration, in which the engagement structure at least substantially overlaps with the body and extends generally toward the transmitting portion relative to the hinge assembly.

2. The device of claim 1, wherein the mounts are adapted to engage and support the user's lower extremities without requiring manual manipulation of the mounts.

3. The device of claim 1, wherein each pair of spaced-apart mounts is adapted to engage and support spaced-apart portions of a respective one of the user's lower extremities.

4. The device of claim 3, wherein one of each pair of mounts is adapted to engage and support a heel portion of the user's lower extremity.

5. The device of claim 3, wherein one of each pair of mounts is adapted to engage and support a foot portion of the user's lower extremity.

6. The device of claim 5, wherein one of each pair of mounts is adapted to engage and support a heel portion of the user's lower extremity.

7. The device of claim 3, wherein each pair of spaced-apart mounts is adapted to accommodate lateral insertion and removal of the user's lower extremities.

8. The device of claim 3, wherein each pair of the spaced-apart mounts includes a stirrup adapted to engage and support a portion of the user's lower extremity.

9. The device of claim 3, wherein at least one of each pair of mounts is rotatable relative to the frame portion.

10. The device of claim 3, wherein the frame portion includes a region to which the pairs of mounts are mounted, and further wherein the region extends at an inclined angle relative to a long axis of the body.

11. The device of claim 1, wherein the device includes a lock mechanism adapted to selectively retain the engagement structure in a selected configuration.

12. The device of claim 11, wherein the lock mechanism is adapted to automatically secure the engagement structure in a selected configuration upon pivoting of the engagement structure to the configuration.

13. The device of claim 11, wherein the lock mechanism includes a release mechanism that upon actuation is adapted to selectively release the lock mechanism to free the engagement structure for pivotal movement relative to the body, and further wherein the release mechanism includes a biasing mechanism that urges the release mechanism away from an actuated position.

14. The device of claim 1, wherein the engagement structure is selectively releasable from the body.

15. The device of claim 1, wherein the engagement structure is non-removably coupled to the body.

16. The device of claim 1, wherein each of the handle assemblies is pivotally coupled to the body.

17. The device of claim 16, wherein the handle assemblies are selectively positionable in a range of configurations that include an extended configuration, in which the handle assemblies extend divergently away from the lower extremity engagement structure, and a collapsed configuration, in which the handle assemblies extend generally parallel to a long axis of the body.

18. The device of claim 16, wherein the device further includes a handle retention structure adapted to limit the degree to which the handle assemblies may pivot away from the body.

19. The device of claim 16, wherein the device further includes at least one retainer adapted to selectively retain the handle assemblies proximate the body.

20. The device of claim 1, wherein each of the handle assemblies is selectively positionable within a range of positions on the body.

21. The device of claim 1, wherein the handle assemblies are coupled to the body by a bracket, and further wherein the bracket is adjustably mounted on the body for selective positioning within a range of positions relative to the lower extremity engagement structure to adjust the distance between the bracket and the lower extremity engagement structure and thereby adjust the distance between the lower extremity engagement structure and the handle assemblies.

22. The device of claim 21, wherein the handle assemblies are pivotally coupled to the bracket.

23. The device of claim 22, wherein the device further includes a handle retention structure adapted to limit the degree to which the handle assemblies may pivot away from the body.

24. The device of claim 23, wherein the device further includes at least one retainer adapted to selectively retain the handle assemblies proximate the body.

25. An isometric exercise device, comprising:

an elongate body defining a long axis;

a lower extremity engagement structure pivotally coupled to an end region of the body and having a plurality of mounts adapted to engage and retain a user's lower extremities, wherein the lower extremity engagement structure is selectively pivotal relative to the body in a range of configurations that includes a collapsed configuration, in which the lower extremity engagement structure at least partially overlaps with the body, and an extended configuration, in which the mounts extend generally away from the body relative to the collapsed configuration;

a transmitting portion associated with the body, wherein the transmitting portion includes a pair of handle assemblies with grippable portions that are adapted to be grasped by a user's hands while the user's lower extremities are engaged by the lower extremity engagement structure such that when a user exerts a caudally directed force upon the grippable portions, the force is transmitted through the grippable portions to exert a tractive force to the user's back, wherein the handle assemblies are pivotally coupled to the body by a bracket and are selectively pivotal within a range of configurations that include a collapsed configuration, in which the handle assemblies extend generally parallel to the long axis, and an extended configuration, in which the handle assemblies extend divergently from the bracket in a direction generally away from the lower extremity engagement structure, and further wherein the bracket is adjustably mounted on the body for selective positioning along the body to respectively adjust the distance between the bracket and the lower extremity engagement structure.

26. The device of claim 25, further including a lock mechanism adapted to selectively retain the lower extremity engagement structure in a selected configuration relative to the body.

27. The device of claim 25, further including a retention structure adapted to limit the degree to which the handle assemblies may pivot away from the long axis of the body.

28. The device of claim 25, wherein the mounts are adapted to engage and support a user's lower extremities without requiring manual manipulation of the mounts.

29. The device of claim 28, wherein the mounts include a pair of stirrup assemblies, and further wherein each stirrup assembly includes a first stirrup that is adapted to engage and support a heel portion of the user's lower extremity proximate the user's ankle and a second stirrup that is adapted to engage and support an upper portion of a user's foot.

30. The device of claim 29, wherein the lower extremity engagement structure includes a frame portion to which the mounts are coupled, and further wherein at least one of the stirrups is rotatably mounted relative to the frame portion.

31. The device of claim 25, wherein the plurality of mounts includes for each of the user's lower extremities at least a pair of spaced-apart mounts adapted to engage and support spaced-apart portions of a respective one of the user's lower extremities.

32. The device of claim 31, wherein one of each pair of mounts is adapted to engage and support a heel portion of the user's lower extremity.

33. The device of claim 31, wherein one of each pair of mounts is adapted to engage and support a foot portion of the user's lower extremity.

34. The device of claim 33, wherein one of each pair of mounts is adapted to engage and support a heel portion of the user's lower extremity.

35. The device of claim 31, wherein each pair of spaced-apart mounts is adapted to accommodate lateral insertion and removal of the user's lower extremities.

36. The device of claim 31, wherein each pair of spaced-apart mounts includes a stirrup adapted to engage and support a portion of the user's lower extremity.

37. The device of claim 31, wherein the engagement structure includes a frame portion that couples each pair of mounts to the body, and further wherein at least one of each pair of mounts is rotatable relative to the frame portion.

38. The device of claim 31, wherein the engagement structure includes a frame portion that couples each pair of mounts to the body, wherein the frame portion includes a region to which each pair of mounts is mounted, and further wherein the region extends at an inclined angle relative to a long axis of the body.

39. The device of claim 26, wherein the lock mechanism is adapted to automatically secure the engagement structure in a selected configuration upon pivoting of the engagement structure to the configuration.

40. The device of claim 26, wherein the lock mechanism includes a release mechanism that upon actuation is adapted to selectively release the lock mechanism to free the engagement structure for pivotal movement relative to the body, and further wherein the release mechanism includes a biasing mechanism that urges the release mechanism away from an actuated position.

41. The device of claim 25, wherein the engagement structure is selectively releasable from the body.

42. The device of claim 25, wherein the engagement structure is non-removably coupled to the body.

43. The device of claim 25, wherein each of the handle assemblies includes at least a pair of adjustable members extending between the bracket and the grippable portion, with the adjustable members adapted to selectively adjust the distance between the grippable portion and the bracket.

44. The device of claim 43, wherein the pair of members are telescoping members that are slidably adjustable relative to each other.

45. An isometric exercise device, comprising:

a body;

a lower extremity engagement structure associated with the body and adapted to engage and retain a user's lower extremities; and a transmitting portion associated with the body generally distal the lower extremity engagement structure, wherein the transmitting portion includes a pair of handle assemblies with grippable portions that are adapted to be grasped by a user's hands while the user's lower extremities are engaged by the lower extremity engagement structure such that when a user exerts a user-directed force upon the grippable portions in a direction generally toward the lower extremity engagement structure, a tractive force is applied to the user's back, wherein each of the handle assemblies is pivotally coupled to the body, and further wherein the device includes a handle retention structure adapted to limit the degree to which the handle assemblies may pivot away from the body.

46. The device of claim 45, wherein the handle assemblies are selectively positionable in a range of configurations that include an extended configuration, in which the handle assemblies extend divergently away from the lower extremity engagement structure, and a collapsed configuration, in which the handle assemblies extend generally parallel to a long axis of the body.

47. The device of claim 45, wherein the device further includes at least one retainer adapted to selectively retain the handle assemblies proximate the body.

48. An isometric exercise device, comprising:

a body;

a lower extremity engagement structure associated with the body and adapted to engage and retain a user's lower extremities; and a transmitting portion associated with the body generally distal the lower extremity engagement structure, wherein the transmitting portion includes a pair of handle assemblies with grippable portions that are adapted to be grasped by a user's hands while the user's lower extremities are engaged by the lower extremity engagement structure such that when a user exerts a user-directed force upon the grippable portions in a direction generally toward the lower extremity engagement structure, a tractive force is applied to the user's back, wherein the handle assemblies are coupled to the body by a bracket, and further wherein the bracket is adapted to be slidably adjusted within a range of positions along the body to adjust the distance between the bracket and the lower extremity engagement structure.

49. The device of claim 48, wherein the handle assemblies are selectively positionable in a range of configurations that include an extended configuration, in which the handle assemblies extend divergently away from the lower extremity engagement structure, and a collapsed configuration, in which the handle assemblies extend generally parallel to a long axis of the body.

50. The device of claim 49, wherein the device further includes a handle retention structure adapted to limit the degree to which the handle assemblies may pivot away from the body.

51. The device of claim 50, wherein the device further includes least one retainer adapted to selectively retain the handle assemblies proximate the body.

52. The device of claim 48, wherein each of the handle assemblies is pivotally coupled to the bracket.

* * * * *